United States Patent
Tamaoki et al.

(10) Patent No.: US 6,255,103 B1
(45) Date of Patent: Jul. 3, 2001

(54) CULTIVATING APPARATUS WITH STERILIZING LAMP

(75) Inventors: Yuichi Tamaoki; Hiroki Busujima; Tetsuya Miyoshi; Tadahisa Saga, all of Gunma (JP)

(73) Assignee: Sanyo Electric Co., Ltd., Osaka (JP)

( * ) Notice: Subject to any disclaimer, the term of this patent is extended or adjusted under 35 U.S.C. 154(b) by 0 days.

(21) Appl. No.: 09/407,240

(22) Filed: Sep. 28, 1999

(30) Foreign Application Priority Data

Sep. 29, 1998 (JP) .................................................. 10-274881
Sep. 29, 1998 (JP) .................................................. 10-274882
Feb. 10, 1999 (JP) .................................................. 11-032814

(51) Int. Cl.⁷ .................................................. C12M 1/00
(52) U.S. Cl. .................................. 435/303.1; 435/303.2; 422/22; 422/24; 422/104; 219/407; 236/3; 237/3; 312/236
(58) Field of Search ............................ 435/303.1, 303.2; 422/22, 24, 104; 219/407, 408, 522; 236/3; 237/3; 312/1, 236

(56) References Cited

U.S. PATENT DOCUMENTS 4,696,902 * 9/1987 Bisconte ................... 435/300
5,049,505    9/1991 Sei ........................ 435/311
6,006,659 * 12/1999 Rosenthal ................. 99/451

FOREIGN PATENT DOCUMENTS 62-238449  * 10/1987 (JP) .
1703679 A1 *  1/1992 (SU) .

OTHER PUBLICATIONS

Patent Abstracts of Japan, vol. 014, No. 386 (C0750), Aug. 21, 1990.

* cited by examiner

Primary Examiner—David A. Redding
(74) Attorney, Agent, or Firm—Darby & Darby

(57) ABSTRACT

A cultivating apparatus designed so that cultivating containers for cultivating cultures can be mounted therein and the inside of the apparatus is hermetically sealed by closing a door of said apparatus to cultivate the cultures, is provided with a sterilizing lamp for emitting light for sterilizing germs such as bacteria, etc. contained in the gas in the apparatus. The sterilizing lamp comprises an ultraviolet lamp for emitting ultraviolet rays in which light of 200 nm or less in wavelength is cut off.

7 Claims, 14 Drawing Sheets

CULTIVATING APPARATUS WITH STERILIZING LAMP

BACKGROUND OF THE INVENTION

1. Field of the Invention

The present invention relates to a cultivating apparatus which is applied to a carbon dioxide gas ($CO_2$) incubator, a multi-gas incubator or the like to cultivate cultures such as cells, microorganisms, etc. while keeping the inside of the apparatus under an aseptic (germ-free) condition.

2. Description of the Related Art

A periodic sterilizing treatment is needed for a cultivating apparatus because cultures must be cultivated while keeping the temperature of the inside of the cultivating apparatus (chamber) and the concentration of carbon dioxide ($CO_2$) to constant values and also keeping the inside of the chamber under an aseptic (germ-free) condition.

Further, in the cultivating apparatus as described above, when a cultivating container in which cultures are stocked is fed into or out of the chamber, the outside air invades into the chamber to thereby causing intrusion of the outside air containing various germs such as bacteria, etc. into the chamber. Since the cultivating apparatus is kept under such an environment that not only cultures, but also various germs are liable to grow, these germs may grow and contaminate the cultures.

There is known a conventional cultivating apparatus in which a germs-removing filter such as HEPA (High Efficiency Particulate Air) filter or the like is disposed to remove germs from gas circulating in the chamber.

Such a conventional cultivating apparatus containing a germs-removing filter has such a risk that once a secondary side of the germs-removing filter is contaminated with germs captured by the filter, the germs-removing/germs sterilizing effects of the filter are remarkably degraded because the germs captured by the germs-removing filter do not die, so that the cultures are contaminated by the germs.

Further, since the pore size of the germs-removing filter is smaller than the size of the germs, a pressure loss at the time when gas passes through the germs-removing filter is large and the germs-removing filter is liable to be clogged with the contaminants.

SUMMARY OF THE INVENTION

The present invention has been implemented in view of the foregoing situation, and has an object to provide a cultivating apparatus which easily sterilize germs contained in gas in the apparatus to surely prevent contamination of the germs into cultures, and also suppress increase of the concentration of ozone contained in the gas in the apparatus.

In order to attain the above object, according to a first aspect of the present invention, there is provided a cultivating apparatus which is designed so that a cultivating container for cultivating cultures can be mounted therein and the inside of the apparatus is hermetically sealed by closing a door of the apparatus to cultivate the cultures, characterized by including a sterilizing lamp for sterilizing the germs contained in the gas in the apparatus.

According to a second aspect of the present invention, in the cultivating apparatus of the first aspect, the sterilizing lamp is disposed so as to be covered by a shielding plate which forms the inside of the apparatus, the shielding plate serving to shield the cultures so that light from the sterilizing lamp is not directly irradiated to the cultures in the apparatus.

According to a third aspect of the present invention, in the cultivating apparatus of the second aspect, the shielding plate comprises an inner plate member which forms the inside of the apparatus and also forms a gas circulating passage in cooperation with the main body of the apparatus, and the sterilizing lamp is disposed in the gas circulating passage so as to be covered by the inner plate member.

According to a fourth aspect of the present invention, in the cultivating apparatus of the first aspect, humidifying water is provided in the apparatus, and the sterilizing lamp is disposed in the neighborhood of the surface of the humidifying water.

According to a fifth aspect of the present invention, the cultivating apparatus of the fourth aspect is further provided with a reflection member which is disposed so as to cover the sterilizing lamp.

According to a sixth aspect of the present invention, in the cultivating apparatus of the first aspect, the sterilizing lamp is disposed in the apparatus so as to irradiate light to the inside of the apparatus.

According to a seventh aspect of the present invention, in the cultivating apparatus of the first aspect of the present invention, the cultivating container is designed to intercept light irradiated to the inside of the apparatus.

According to an eighth aspect of the present invention, in the cultivating apparatus of the first aspect of the present invention, the sterilizing lamp is turned on/out interlockingly with an open/close operation of the door.

According to a ninth aspect of the present invention, in the cultivating apparatus of the eight aspect, the sterilizing lamp is turned out when the door is opened, and turned on for a predetermined time after the door is closed.

According to a tenth aspect of the present invention, in the cultivating apparatus of the first aspect of the present invention, the sterilizing lamp repeats the turn-on/turn-out operation.

According to an eleventh aspect of the present invention, in the cultivating apparatus of the first aspect of the present invention, the sterilizing lamp is an ultraviolet lamp.

According to a twelfth aspect of the present invention, in the cultivating apparatus of the eleventh aspect, the ultraviolet lamp is designed so that light of 200 nm or less in wavelength is suppressed (cut off).

The cultivating apparatus according to the first or sixth aspect of the present invention has the following effect.

The apparatus is provided with the sterilizing lamp for sterilizing germs contained in gas in the apparatus, and thus the germs contained in the gas can be easily sterilized by light irradiated from the sterilizing lamp, so that the contamination of the germs into cultures can be surely prevented.

The cultivating apparatus according to the second or third aspect of the present invention has the following effect.

The sterilizing lamp is disposed so as to be covered by the shielding plate, and the light irradiated from the sterilizing lamp is intercepted and prevented from being irradiated to the inside of the apparatus by the shielding plate, so that the light irradiated from the sterilizing lamp is not directly irradiated to the cultures being cultivated in the cultivating container disposed in the apparatus. Therefore, the cultures can grow in the cultivating container without being adversely effected.

The cultivating apparatus according to the fourth or fifth aspect of the present invention has the following effect.

The humidifying water is provided in the apparatus, and the sterilizing lamp is disposed in the neighborhood of the surface of the humidifying water. Therefore, not only gas circulating in the apparatus (chamber), but also the humidifying water can be subjected to a sterilizing treatment.

Further, the sterilizing lamp is covered by the reflection member to sterilize the humidifying water in a wide range, and also the light from the sterilizing lamp is prevented from being directly irradiated to the inside of the chamber. Further, evaporation of water on a water plate 38 can be promoted by heat of the turn-on ultraviolet lamp 30.

The cultivating apparatus according to the seventh aspect of the present invention has the following effect.

The cultivating container is designed to intercept the light from the sterilizing lamp, and thus even when the light is irradiated from the sterilizing lamp into the apparatus, the light is prevented from being directly irradiated to the cultures being cultivated in the cultivating container. Therefore, the cultures can grow without being adversely effected.

The cultivating apparatus according to the eighth aspect of the present invention has the following effect.

Since the turn-on/turn-out operation of the sterilizing lamp is carried out interlockingly with the open/close operation of the door, even when the door is opened to cause invasion of germs such as germs, microorganisms, etc. into the apparatus, the sterilizing lamp is turned on after the door is closed, thereby quickly sterilizing the invading germs by the light irradiated from the sterilizing lamp.

The cultivating apparatus according to the ninth aspect of the present invention has the following effect.

The sterilizing lamp is designed to be turned on for a predetermined time after the door is closed, so that the germs invading into the apparatus due to the door opening operation can be quickly sterilized, and also the composition variation of gas and the increase of the temperature of the inside of the apparatus can be suppressed by turning on the sterilizing lamp for a long time. In addition, the lifetime of the sterilizing lamp can be increased and the power consumption can be reduced.

The cultivating apparatus according to the tenth aspect of the present invention has the following effect.

The sterilizing lamp is repetitively and alternately turned on and out under the door-closed state, so that the gas in the apparatus is sterilized and the aseptic (germ-free) condition can be excellently kept in the apparatus.

In addition, the sterilizing lamp is not continuously turned on under the door-closed state, so that the composition variation of the gas and the increase of the temperature in the apparatus can be suppressed. In addition, the lifetime of the sterilizing lamp can be enhanced and the power consumption can be reduced.

The cultivating apparatus according to the eleventh or twelfth aspect of the present invention has the following effect.

The cultivating apparatus is provided with the ultraviolet lamp for sterilizing germs contained in gas in the apparatus, and the germs contained in the gas can be sterilized by ultraviolet rays irradiated from the ultraviolet lamp, so that the germs can be prevented from being contaminated into cultures.

Further, light of 200 nm or less in wavelength is suppressed (cut off) from the ultraviolet rays of the ultraviolet lamp, so that occurrence of ozone due to the irradiation of the ultraviolet rays can be suppressed. As a result, the increase of the concentration of ozone in the gas in the apparatus can be suppressed, and the cultures can grow in the cultivating container mounted in the apparatus without being adversely effected.

DETAILED DESCRIPTION OF THE PREFERRED EMBODIMENTS

Preferred embodiments according to the present invention will be described with reference to the accompanying drawings.

[A] First Embodiment

Figure 1:
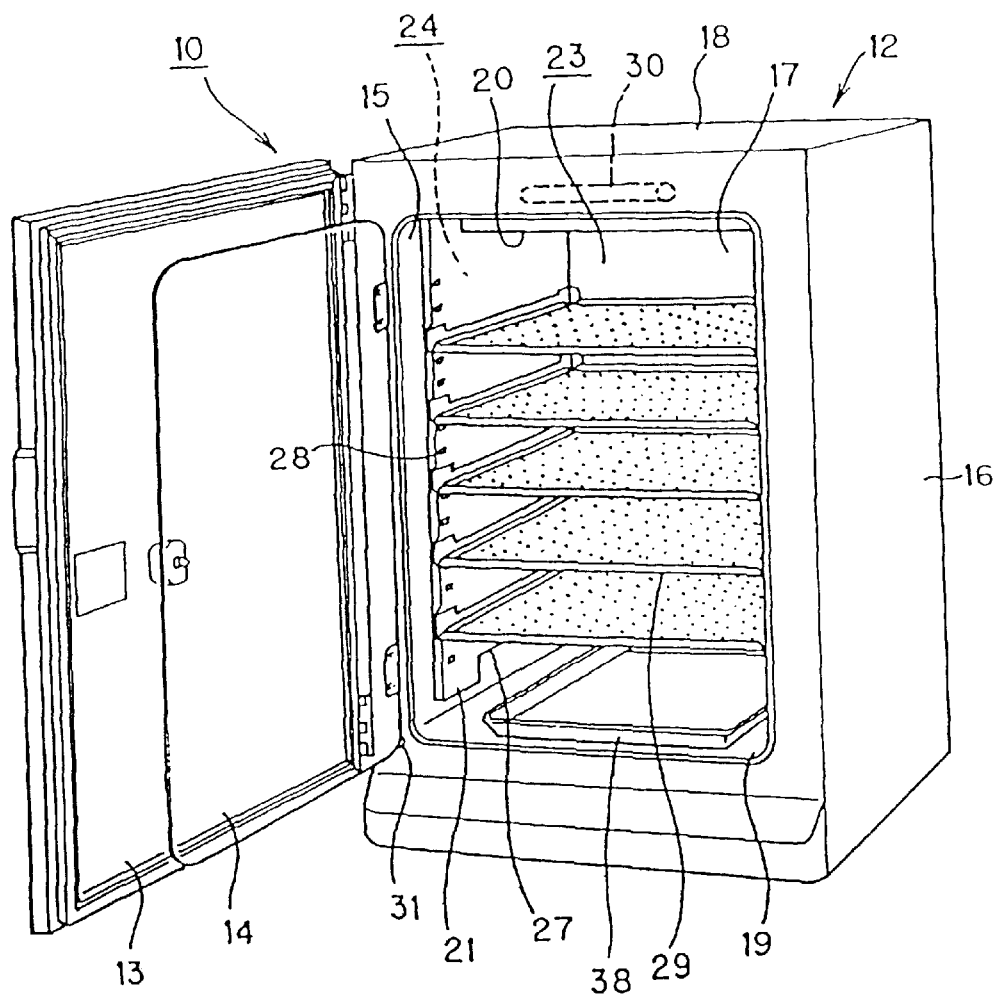
FIG. 1 is a perspective view showing a carbon dioxide ($CO_2$) incubator to which a first embodiment of a cultivating apparatus of the present invention is applied.

FIG. 1 is a perspective view showing a carbon dioxide gas ($CO_2$) to which a first embodiment of a cultivating apparatus of the present invention is applied.

As shown in FIG. 1, a carbon dioxide gas ($CO_2$) incubator 10 as a cultivating apparatus is used to cultivate cultures (cells, microorganisms, etc.) which are stocked together with culture liquid and culture medium in a cultivating container 11 (FIG. 3) such as a laboratory dish or the like.

The incubator 10 includes a main body 12 having an opening in the front surface thereof. An outer door 13 and an inner door 14 are secured to the main body 12 so as to freely open/close the opening of the main body 12. When the outer door 13 is closed, the incubator is kept airtight.

Figure 2:
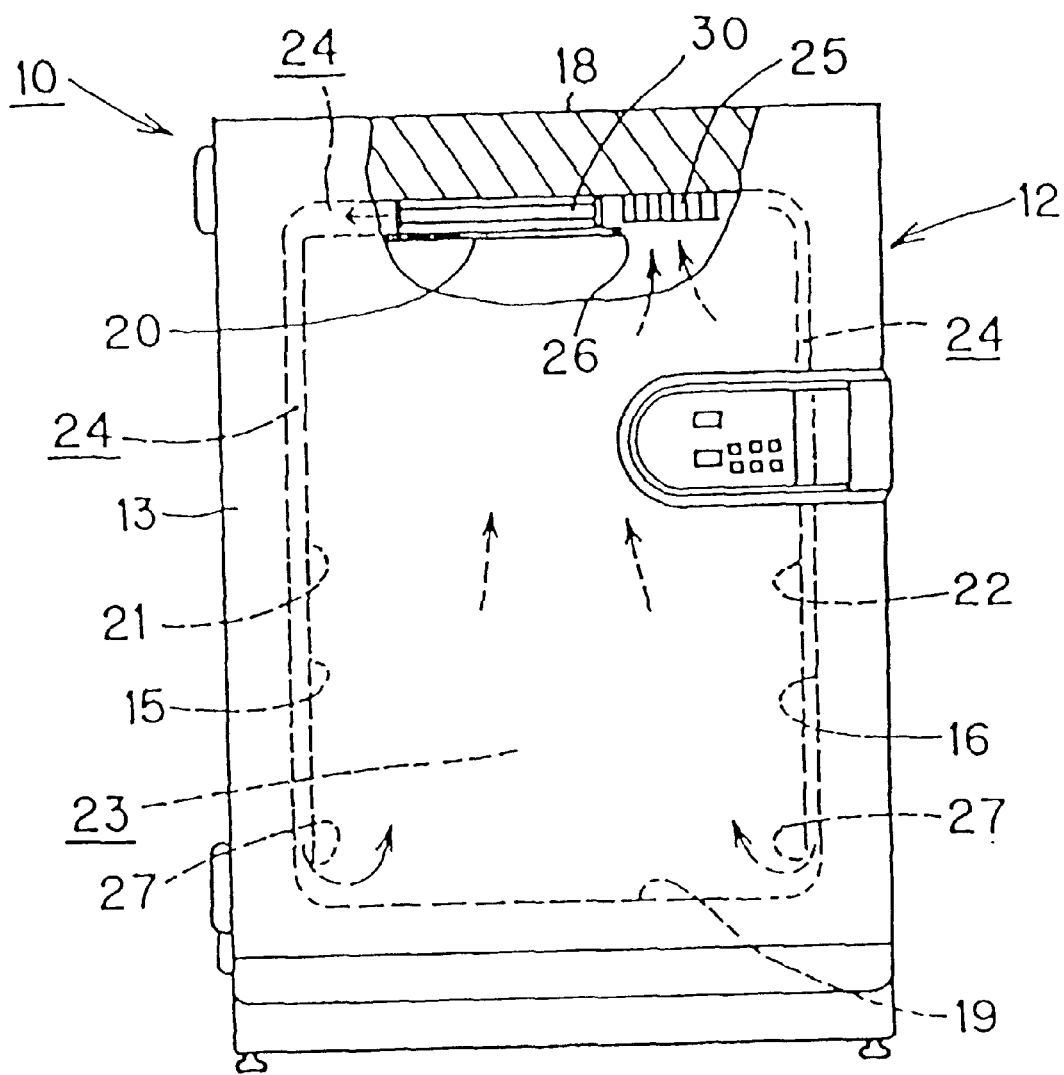
FIG. 2 is a front view of the carbon dioxide incubator of FIG. 1 when a door of the incubator is closed.

As shown in FIGS. 1 and 2, the main body 12 is constructed by integrally fabricating and joining a pair of confronting side walls 15 and 16, a back wall 17, a top wall 18 and a bottom wall 19. The side walls 15, 16, the back wall 17, the top wall 18, the bottom wall 19 and the outer door 13 are designed in an adiabatic structure.

A top plate portion 20 serving as a shielding plate or inner plate member is disposed at the inside of the top wall 18, and side plates 21, 22 each serving as a shielding plate or inner plate member are disposed at the inside of both the side walls 15, 16 so as to be continuously joined to the top plate portion 20. The top plate potion 20, the side plates 21 and 22, the top wall 18, the side walls 15 and 16, the back wall 17 and the bottom wall 19 form a chamber 23 (an inner space of the apparatus) as the inside of the apparatus of the incubator 10.

The space between the top plate portion 20 and the top wall 18, the space between the side wall 15 and the side plate 21 and the space between the side wall 16 and the side plate 22 intercommunicate with one another to form a gas circulating passage 24. A fan 25 is disposed between the top plate portion 20 and the top wall 18 in the gas circulating passage 24. By driving the fan 25, gas in the chamber 23 is sucked from a suck-in port 26 formed in the top plate portion 20 into the gas circulating passage 24. The gas thus sucked in flows along a direction indicated by a broken line of FIG. 2 in the gas circulating passage 24, and then blown out from a blow-out port 27 formed at the lower edges of the side plates 21 and 22 into the chamber 23.

As described above the gas in the chamber 23 flows upwardly in the chamber 23 by driving the fan 25, and circulates in the chamber 23 and the gas circulating passage 24. Through the circulation of the gas, the temperature of the gas circulating passage 24, the concentration of carbon dioxide gas ($CO_2$), etc. are adjusted so as to be suitable for growth of cultures. The fan 25 is stopped when the outer door 13 is opened so that the outside air hardly invades into the chamber 23.

Figure 3:
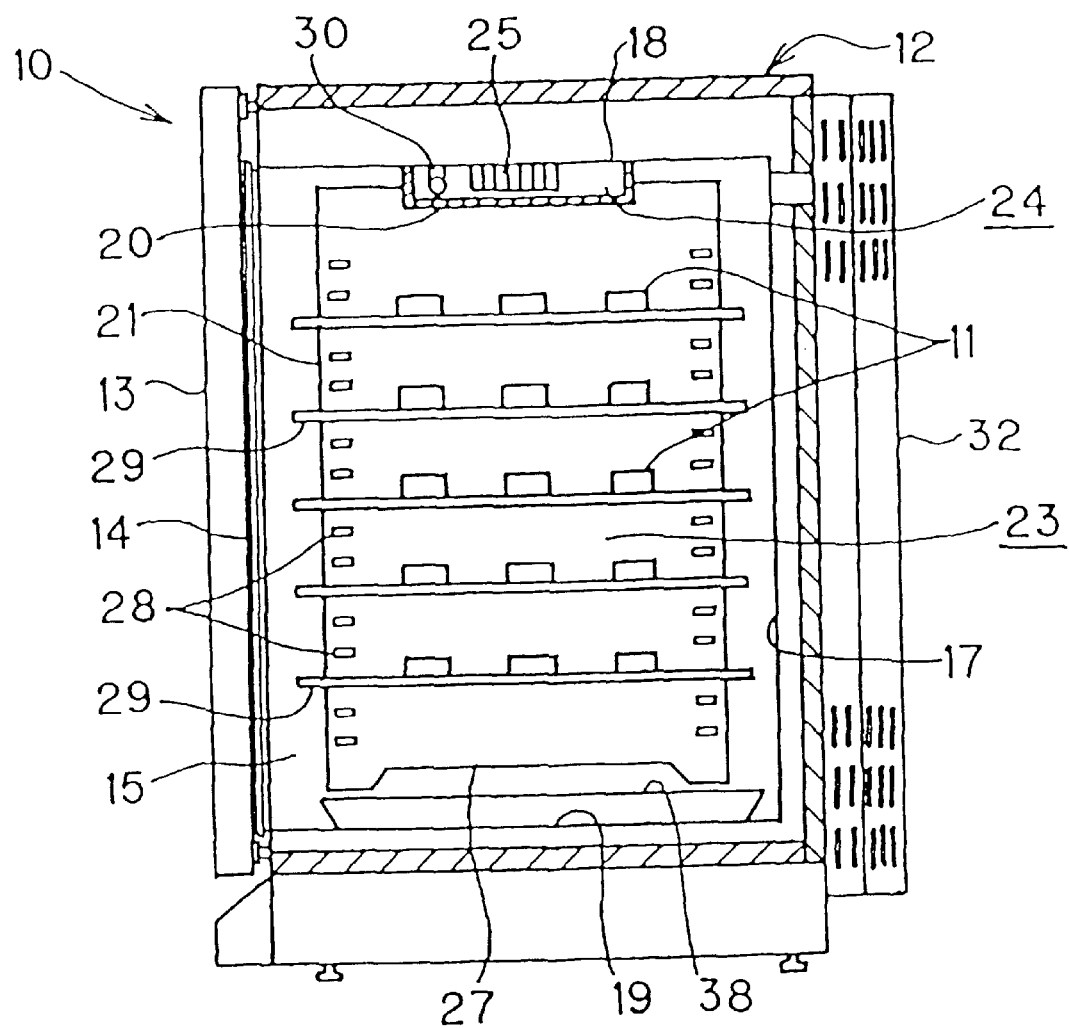
FIG. 3 is an explanatory diagram (side sectional view) showing the carbon dioxide incubator of FIG. 1 when the door of the incubator of FIG. 1 is closed.
Figure 4:
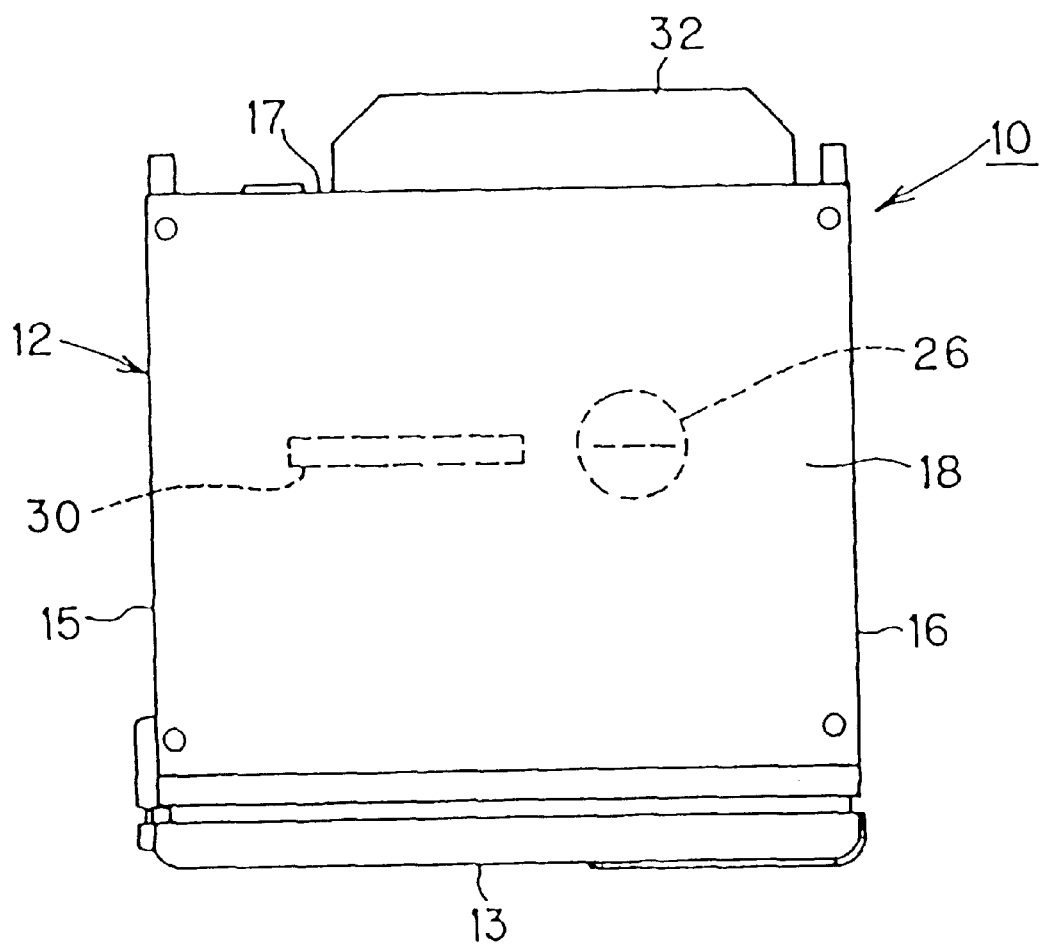
FIG. 4 is a plan view showing the carbon dioxide incubator of FIG. 1 when the door of the incubator of FIG. 1 is closed.

A plurality of support holes 28 are formed in the vertical direction in a pair of confronting side plates 21, 22, and a plurality of shelves 29 are supported in the horizontal direction in the chamber 23 so that both ends of each shelf 29 is fitted in each support holes. Cultivating containers are mounted on these shelves 29 as shown in FIG. 3. Each cultivating container 11 is fed out from the chamber 23 or fed into the chamber 23 and mounted on the selves when the outer door 13 and the inner door 14 are opened.

Reference numeral 38 of FIG. 1 represents a water dish in which water is put to humidify the gas in the chamber 23.

An ultraviolet lamp 30 serving as a sterilizing lamp is disposed between the top plate portion 20 and the top wall 18 in the gas circulating passage 24. With the ultraviolet lamp 30, the gas flowing in the gas circulating passage is exposed to ultraviolet rays as light to sterilize various germs contained in the gas. As describe above, the ultraviolet rays from the ultraviolet lamp 30 sterilizes the various germs contained in the gas and reduce the amount of the germs, thereby keeping the inside of the chamber 23 under a germ-free condition.

Since the ultraviolet lamp 30 is disposed in the gas circulating passage 24 so as to be covered by the top plate portion 20, the ultraviolet rays from the ultraviolet lamp 30 are intercepted by the top plate portion 20, so that no ultraviolet ray is directly irradiated to the inside of the chamber 23.

Further, the rays of 200 nm or less in. wavelength are reduced from the ultraviolet rays from the ultraviolet lamp 30 by an optical filter or the like. Therefore, occurrence of ozone due to irradiation of ultraviolet rays to the gas in the gas circulating passage 24 can be suppressed. As a result, even when the ultraviolet lamp 30 is turned on, the concentration of ozone in the gas within the chamber 23 can be prevented from increasing.

Figure 5:
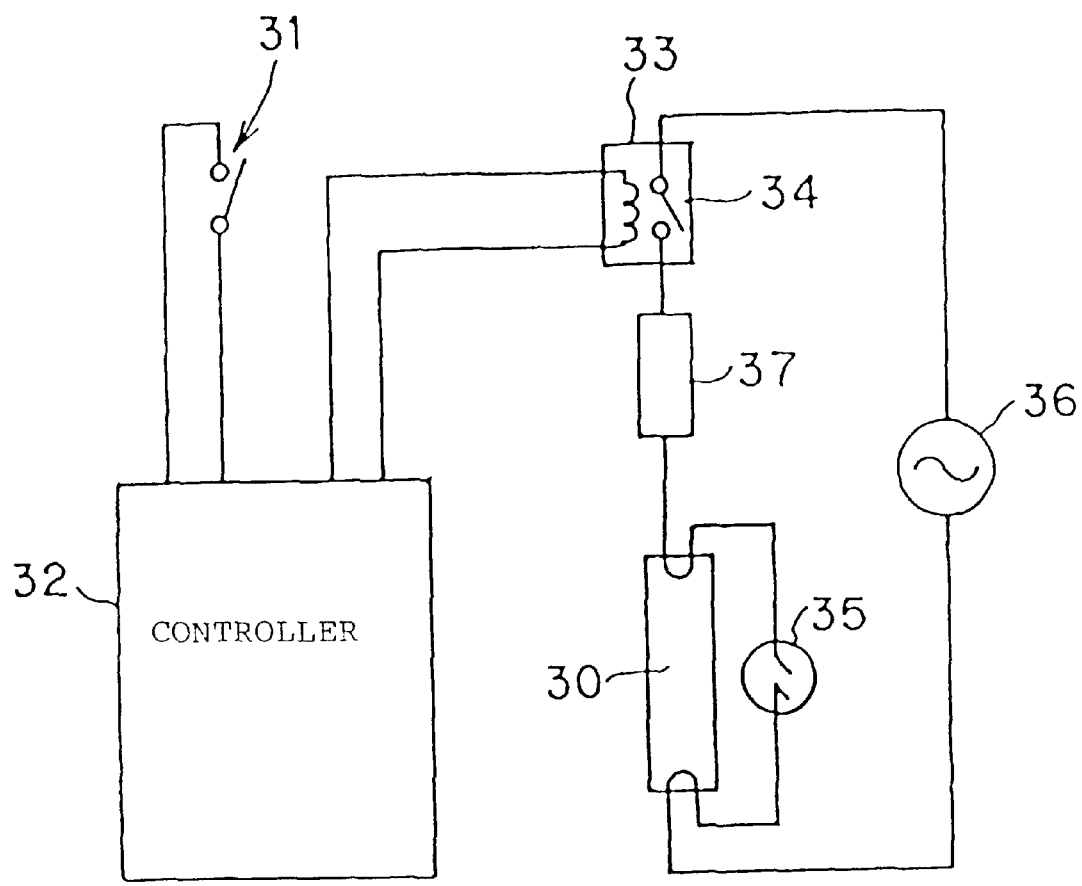
FIG. 5 is a diagram showing an electrical circuit for controlling a turn-on operation of a ultraviolet lamp in the incubator of FIG. 1.

Further, the ultraviolet lamp 30 is turned on/out interlockingly with the open/close operation of the outer door 13. Specifically, as shown in FIG. 1, a lamp switch 31 is disposed so as to abut against the outer door 13 when the closing operation of the outer door 13 is carried out. The controller 32 (FIG. 3) mounted at the outside of the back wall 17 of the main body 12 of the apparatus controls a relay switch 34 of a relay 33 to carry out ON operation as shown in FIG. 5 when the closing operation of the outer door 13 is carried out and the lamp switch 31 is turned on, and a glow starter acts to apply a voltage from a power source 36 to the ultraviolet lamp 30 through a stabilizer 37 to turn on the ultraviolet lamp 30. When the opening operation of the outer door 13 is carried out and the lamp switch 31 is turned off, the controller 32 turns off the relay switch 34 of the relay 33 to turn out the ultraviolet lamp 30.

The ultraviolet lamp 30 is continued to be turned on for a predetermined time (for example, 5 minutes) from the time when the closing operation of the outer door 13 is carried out, thereby sterilizing various germs which invade into the chamber 23 when the opening operation of the outer door 13 is carried out.

Further, the turn-on/out operation of the ultraviolet lamp 30 may be repetitively carried out while the outer door 13 is kept to be closed for a long term. For example, the controller 32 may control the ultraviolet lamp 30 to be turned on for a predetermined time (for example, 5 minutes) at a fixed time interval (for example, 2 hours) under the long-term closed state of the outer door 13. The repetitive turn-on operation of the ultraviolet lamp 30 under the long-term closed state of the outer door 13 periodically sterilizes the germs in the chamber 23 of the incubator 10, so that the inside of the chamber 23 is kept under the aseptic condition. The fixed time interval (turn-out time) and the predetermined time (turn-on time) may be set to any values.

When the controller 32 does not continuously turn on the ultraviolet lamp 30 when the outer door 13 is kept to be closed, both of the increase of the temperature of the chamber 23 and composition variation caused by occurrence of ozone due to irradiation of ultraviolet rays can be suppressed. In addition, the lifetime of the ultraviolet rays can be enhanced, and the power consumption can be reduced.

Therefore, according the present invention, the following effects (1) to (7) can be achieved.

(1) The incubator 10 is provided with the ultraviolet lamp 30 for sterilizing various germs contained in gas in the chamber 23. Therefore, the germs contained in the gas in the chamber 23 can be easily sterilized by the ultraviolet rays irradiated from the ultraviolet lamp 30, and thus the contamination of various germs in cultures can be surely prevented.

(2) Since the ultraviolet lamp 30 is disposed in the gas circulating passage 24 so as to be covered by the top plate portion 20 and thus the ultraviolet rays from the ultraviolet lamp 30 is prevented from being irradiated into the chamber 23, the ultraviolet rays from the ultraviolet lamp 30 is prevented from being directly irradiated to the cultures cultivated in the cultivating containers 11 mounted in the chamber 23. Therefore, no adverse effect is imposed on the growth of the cultures.

(3) The turn-on/out operation of the ultraviolet lamp 30 is carried out interlockingly with the open/close operation of the outer door 13. Therefore, even when various germs invade into the chamber 23 due to the open operation of the outer door 13, the ultraviolet lamp 30 is turned on after the closing operation of the outer door 13 is carried out, and the invading germs can be quickly sterilized by the ultraviolet rays irradiated from the ultraviolet lamp 30.

(4) The ultraviolet lamp 30 is designed to be turned on for a predetermined time after the closing operation of the outer door 13 is carried out. Therefore, various germs invading into the chamber 23 due to the opening operation of the outer door 13 can be quickly sterilized by the ultraviolet rays from the ultraviolet lamp 30, and also occurrence of ozone and increase of the temperature of the chamber 23 which would be caused by the long-term turn-on operation of the ultraviolet lamp 30 can be suppressed. In addition, the lifetime of the ultraviolet lamp 30 can be enhanced and the power consumption can be reduced.

(5) Since the ultraviolet lamp 30 is designed to be repetitively turned on and off under the long-term closed state of the outer door 13, gas in the chamber 23 is sterilized to keep the inside of the chamber 23 under a aseptic condition.

(6) Since the ultraviolet lamp 30 is prohibited from being continuously turned on under the long-term closed state of the outer door 13, occurrence of ozone and increase of the temperature of the inside of the chamber 23 can be suppressed, and further the enhancement of the lifetime of the ultraviolet lamp 30 and the reduction of the power consumption can be attained.

(7) Since light of 200 nm or less in wavelength is reduced from light irradiated from the ultraviolet lamp 30, so that occurrence of ozone due to the ultraviolet rays irradiated from the ultraviolet lamp 30 can be suppressed. Therefore, increase of the concentration of ozone contained in the gas in the chamber 23 can be suppressed, thereby preventing the growth of cultures in the cultivating containers 11 mounted in the chamber 23 from being adversely effected by ozone.

[B] Second Embodiment

Figure 6:
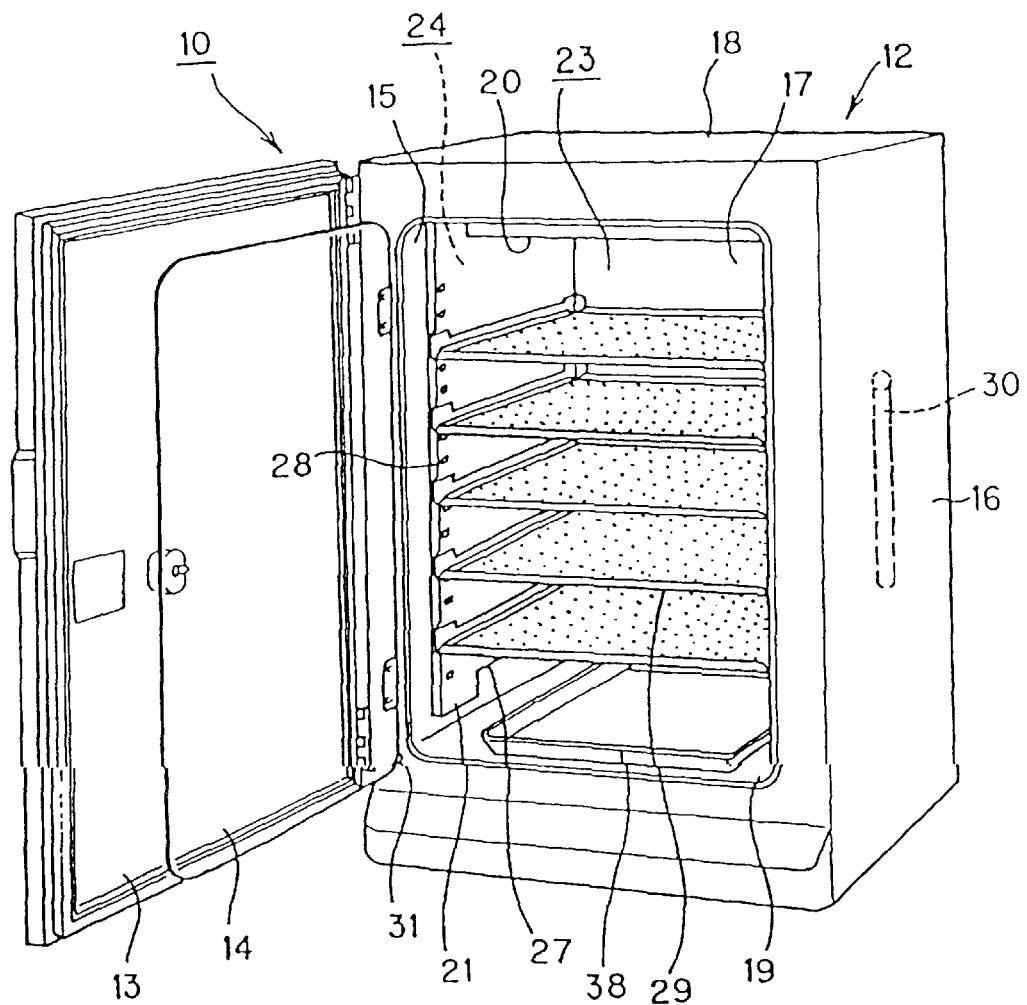
FIG. 6 is a perspective view showing a carbon dioxide ($CO_2$) incubator to which a second embodiment of the cultivating apparatus of the present invention is applied.
Figure 7:
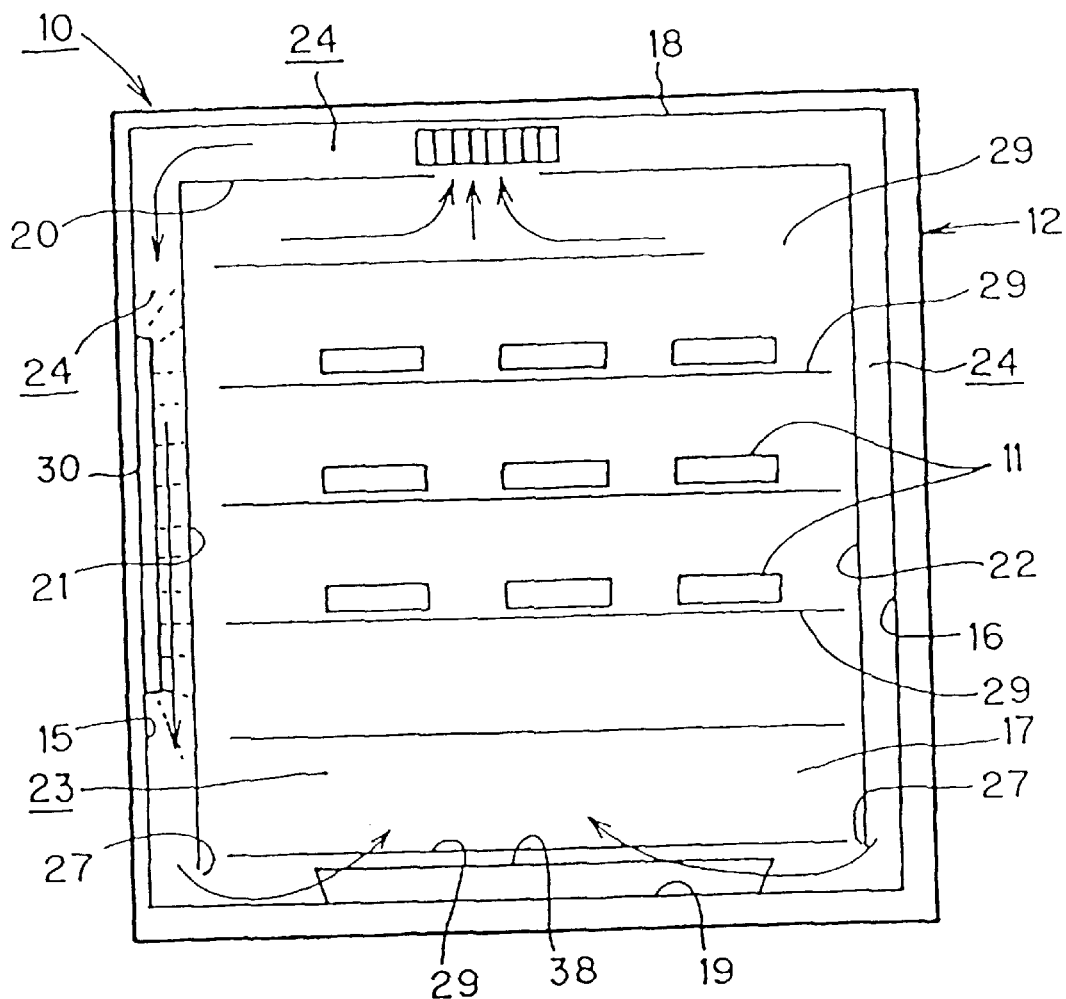
FIG. 7 is a front view showing the carbon dioxide incubator when the door of the incubator of FIG. 6 is opened.

FIGS. 6 and 7 are perspective view and explanatory diagram (side sectional view) showing a carbon dioxide gas ($CO_2$) gas to which a second embodiment of the cultivating apparatus of the present invention is applied. In the second embodiment, the same elements as the first embodiment are represented by the same reference numerals, and the description on these elements is omitted from the following description.

In the carbon dioxide gas ($CO_2$) incubator 10 serving as the cultivating apparatus of the second embodiment, the ultraviolet lamp 30 is disposed in the gas circulating passage 24 between the side plate 21 and the side wall 15. The ultraviolet rays emitted from the ultraviolet lamp 30 sterilizes and reduces various germs contained in gas in the chamber 23, thereby keeping the inside of the chamber 23 under an aseptic condition.

Here, since the ultraviolet lamp 30 is covered by the side plate 21, the second embodiment has the same effect as the first embodiment in that the ultraviolet rays emitted from the ultraviolet lamp 30 are intercepted by the side plate 21 and the inside of the chamber 23 is prevented from being exposed to the ultraviolet rays.

Accordingly, the second embodiment also has the foregoing effects (1) to (7).

[C] Third Embodiment

Figure 8:
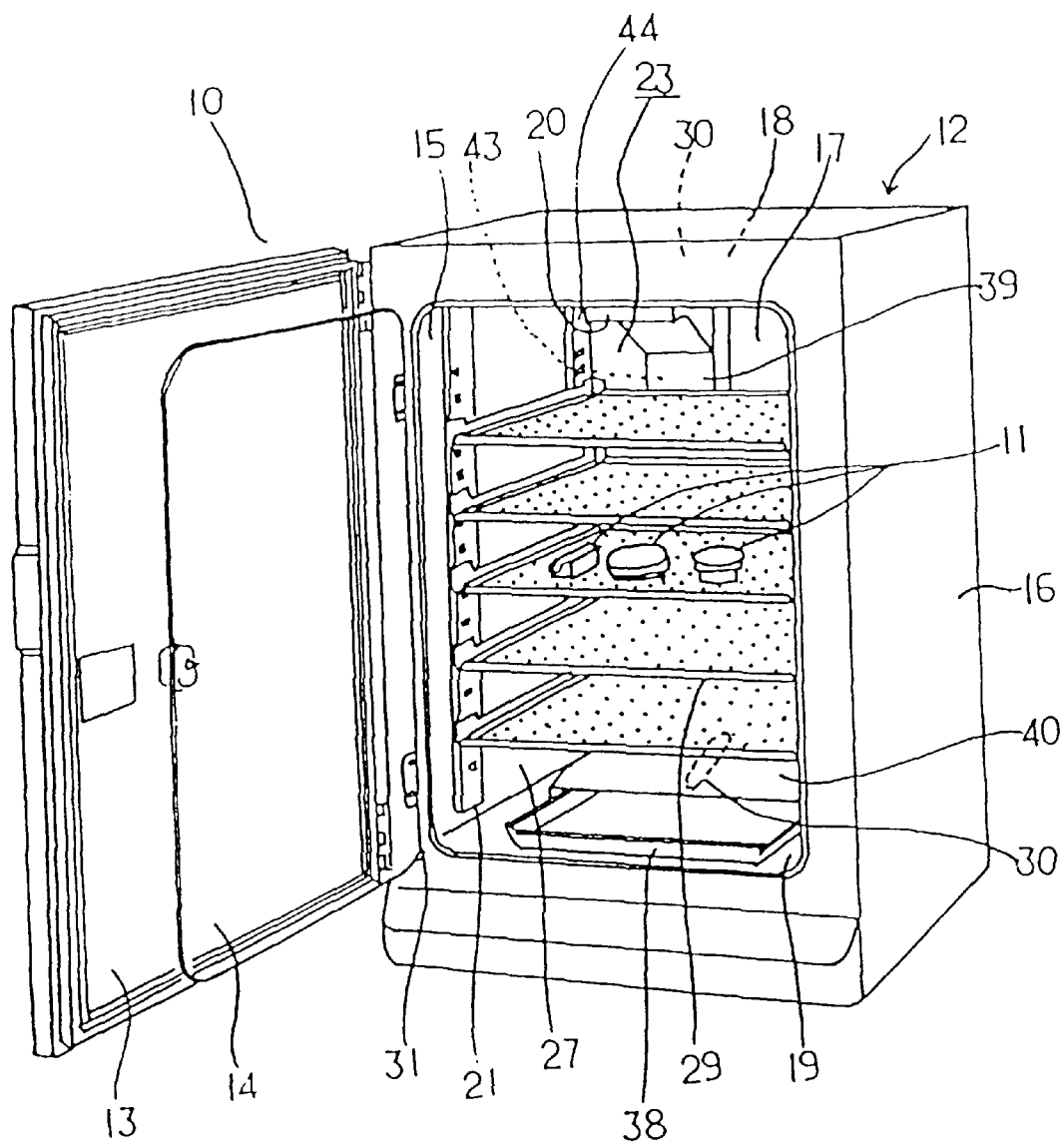
FIG. 8 is a perspective view showing a carbon dioxide gas ($CO_2$) incubator to which a third embodiment of the cultivating apparatus of the present invention is applied.
Figure 9:
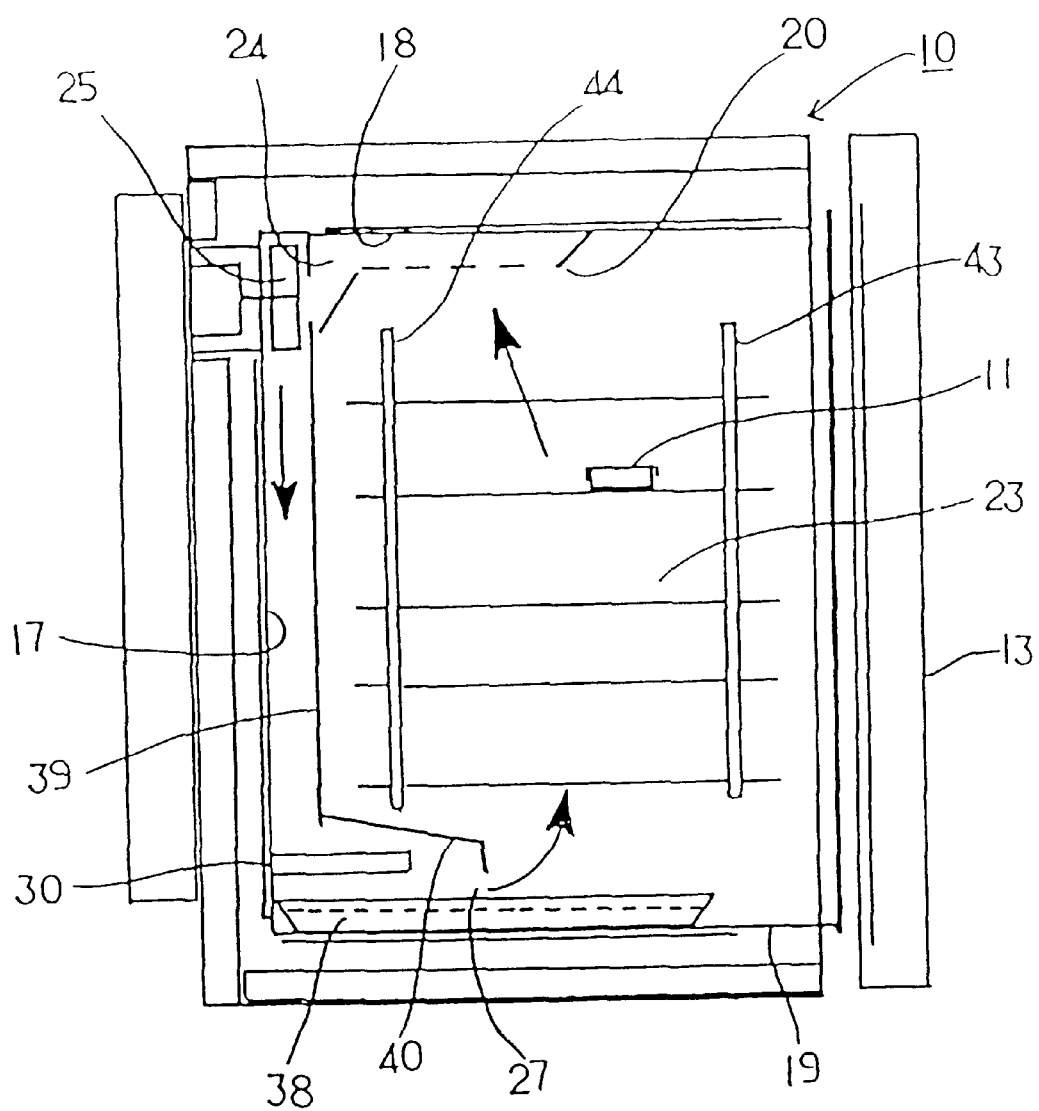
FIG. 9 is an explanatory diagram (side sectional view) showing the carbon dioxide gas incubator when the door of the incubator is closed.
Figure 10:
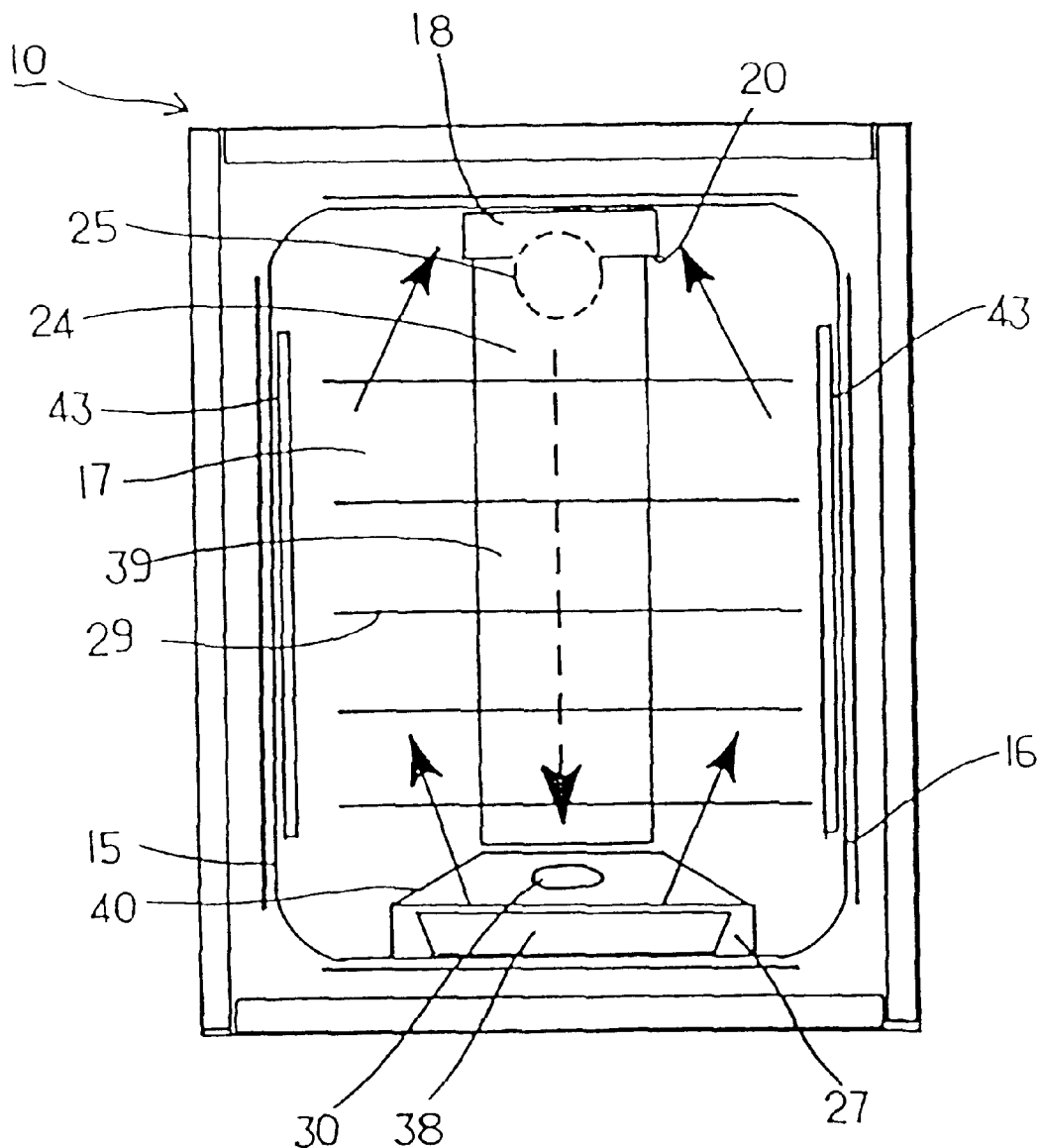
FIG. 10 is a front view showing the carbon dioxide gas incubator of FIG. 8 when the door of the incubator is opened.

FIG. 8 is a perspective view showing a carbon dioxide gas ($CO_2$) incubator to which a third embodiment of the cultivating apparatus of the present invention is applied, FIG. 9 is an explanatory diagram (side sectional view) showing the incubator of FIG. 8 when the door of the incubator is closed, and FIG. 10 is an explanatory diagram (front view) showing the incubator of FIG. 8 when the door of the incubator is opened. In the third embodiment, the same elements as the first and second embodiments are represented by the same reference numerals.

In the cultivating apparatus 10 of this embodiment, a back plate 39 is disposed at the back wall 17 to form a space between the back plate 39 and the back wall 17 so that the space intercommunicates with the gas circulating passage 24 between the top plate portion 20 and the top wall 18. The fan 25 is provided between the back wall 17 and the back plate 39 so that the gas in the space between the top plate portion 20 and the top wall 18 is sucked and then discharged to the space between the back wall 17 and the back plate 39, whereby the gas in the chamber is circulated.

Two pairs of shelf supporting poles 43, 44 are provided at the inner sides of the side walls 15, 16 so as to confront each other. Plural support holes 28 are formed in the vertical direction in the shelf support poles 43, 44, and plural shelves 29 are suspended in the horizontal direction over the shelf support poles 43, 44 in the chamber 23 by engaging both the ends of each shelf 29 into the support holes 28. As shown in FIG. 8, cultivating containers are mounted on these shelves 29.

In this embodiment, the ultraviolet lamp 30 is disposed at the exit of the gas circulating passage 24, that is, at the lower portion of the space between the back wall 17 and the back plate 39 so as to be located near above the water dish 38 in which humidifying water is stocked. Therefore, the ultraviolet rays from the ultraviolet lamp 30 sterilizes various germs contained in the circulated gas, and also are irradiated to the humidifying water stocked in the water dish 38, so that various germs contained in the humidifying water can be also sterilized and the water in the water dish 38 can be promoted to be vaporized by the heat of the turned-on ultraviolet lamp 30.

Further, the ultraviolet lamp 30 is covered by a reflection member 40 provided at the exit side of the gas circulating passage 24. The reflection member 40 serves to prevent the ultraviolet rays of the ultraviolet lamp 30 from being directly irradiated to the inside of the cultivating apparatus, and also it is designed so that at least the inner surface thereof reflects the ultraviolet rays. Therefore, the humidifying water in the water dish 38 can be subjected to the sterilization treatment over a wide area.

Various methods may be used to reflect the ultraviolet rays. For example, at least the inner surface of the reflection member 40 may be subjected to a mirror-finishing treatment, formed of metal material or subjected to a plating-finishing treatment. When the reflection member is formed of metal material, use of stainless material brings an effect, however, use of aluminum brings a larger effect because aluminum has a higher reflection efficiency to ultraviolet rays.

Accordingly, the third embodiment has the following effects (8) to (10) in addition to the above effects (1) to (7).

(8) Various germs are liable to grow in water. However, since the ultraviolet lamp 30 is disposed nearly above the water dish 38 in the third embodiment, both of the gas in the chamber 23 and the humidifying water in the water dish 38 can be subjected to the sterilization treatment.

(9) Further, since the ultraviolet lamp 30 is covered by the reflection member 40, irradiation of ultraviolet rays into the cultivating apparatus can be prevented, and also the ultraviolet rays can be irradiated to the water dish 38 over a wide area, so that the sterilization efficiency can be enhanced.

(10) The evaporation of the water in the water dish 38 can be promoted by the heat of the turn-on ultraviolet lamp 30.

[D] Fourth Embodiment

Figure 11:
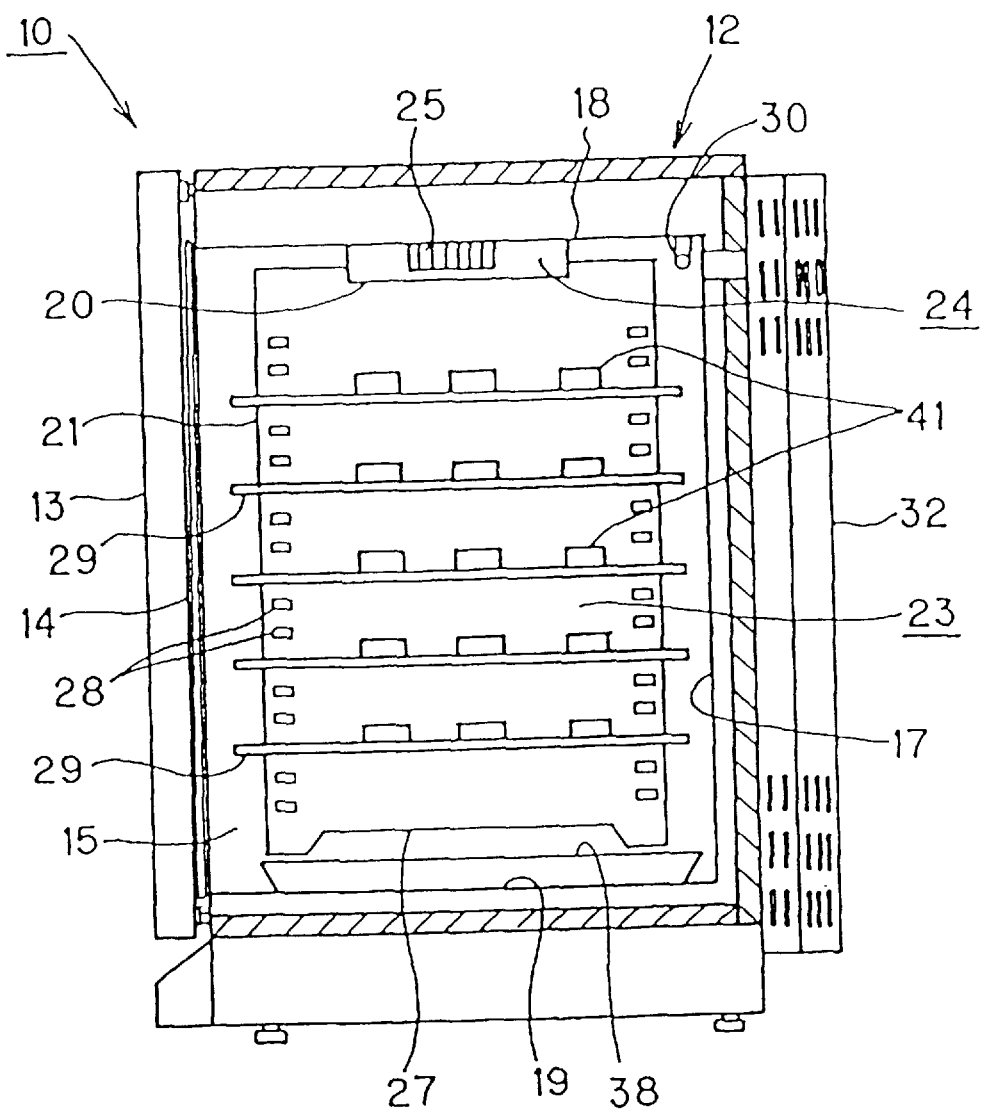
FIG. 11 is an explanatory diagram (side sectional view) showing a carbon dioxide gas ($CO_2$) incubator to which a fourth embodiment of the cultivating apparatus of the present invention is applied when the door of the incubator is closed.
Figure 12:
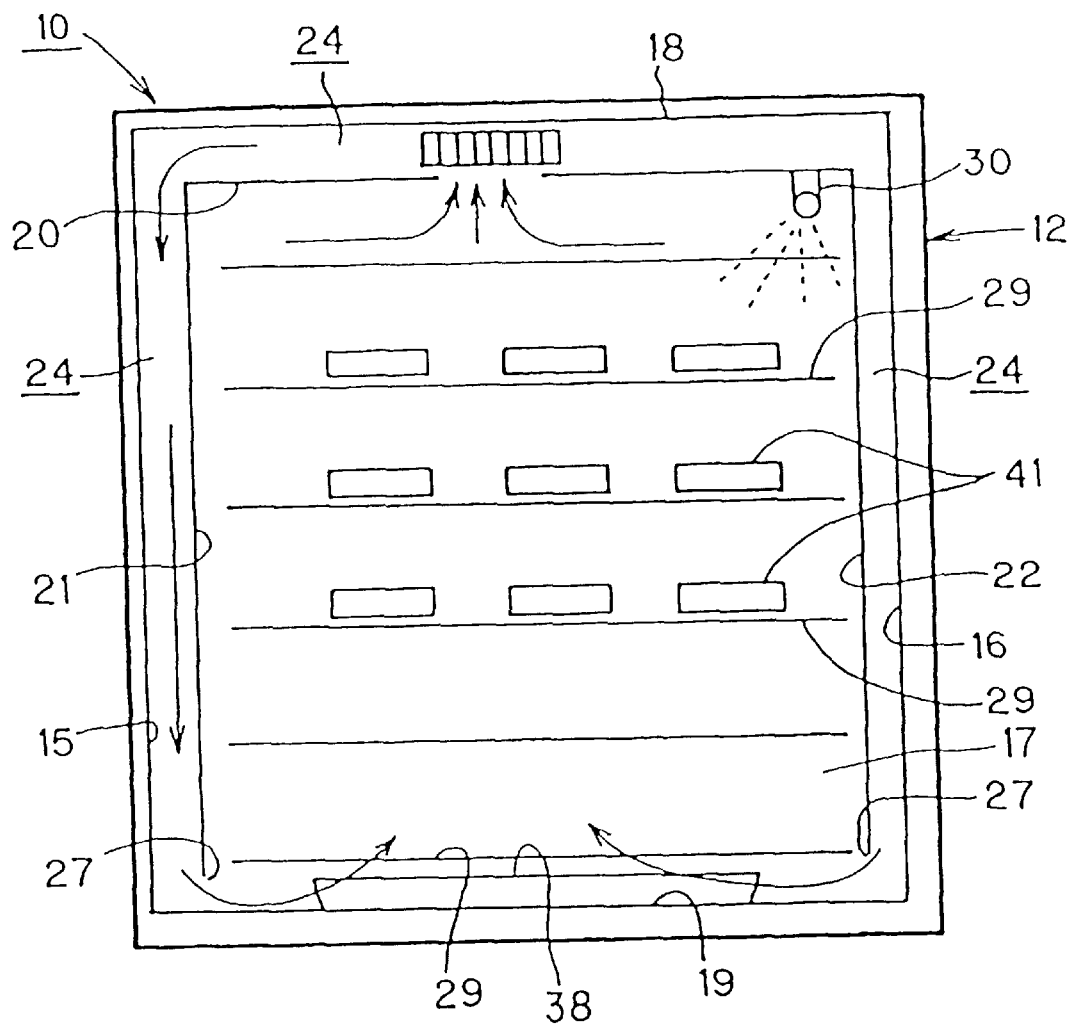
FIG. 12 is front view showing the carbon dioxide gas incubator of FIG. 11 when the door of the incubator is opened.

FIG. 11 shows a carbon dioxide gas ($CO_2$) incubator to which a fourth embodiment of the cultivating apparatus of the present invention is applied, and FIG. 12 is a front view of the incubator of FIG. 11 when the outer door 13 is opened. In the fourth embodiment, the same elements as the first to third embodiments are represented by the same reference numerals, and the duplicative description thereof is omitted.

In the carbon dioxide gas ($CO_2$) incubator 10 as the cultivating apparatus in the fourth embodiment, the ultraviolet lamp 30 is not disposed in the gas circulating passage 24, but disposed in the chamber 23 so that the ultraviolet rays from the ultraviolet lamp 30 are directly directed to the inside of the chamber 23. FIG. 11 shows a case where the ultraviolet lamp 30 is provided at the side of the back wall 17, and FIG. 12 shows a case where the ultraviolet lamp 30 is provided at the side of the side wall 22. As described above, the ultraviolet lamp 30 may be provided at any position in the chamber 23. Ultraviolet rays are irradiated to the ultraviolet lamp 30 while cutting off light (ultraviolet rays) of 200 nm or less in wavelength.

Further, in the fourth embodiment, cultivating containers in which cultures are cultivated (grow) are formed of ultraviolet-ray intercepting material through which no ultraviolet ray is transmitted. Alternatively, the cultivating containers 41 may be designed so that the surface or back surface of constituting material such as glass material or the lie which constitute the cultivating containers 41 may be coated with ultraviolet-ray intercepting coating through which no ultraviolet ray is transmitted (the glass material has generally an inherent characteristic that ultraviolet rays are hardly transmitted therethrough, and thus it may be used alone. However, it is preferable to coat the glass material with material or coating through which no ultraviolet ray is transmitted). As described above, the cultivating containers 41 themselves are designed so as to intercept the ultraviolet rays irradiated from the ultraviolet lamp 30, so that no ultraviolet ray is directly irradiated to the cultures stocked in the cultivating containers 41.

Accordingly, according to the fourth embodiment of the present invention, the following effect (11) is achieved in addition to the effects (1), (3) to (7) of the first embodiment.

(11) The cultivating containers 41 mounted in the chamber 23 of the incubator 10 are designed so as to intercept ultraviolet rays. Therefore, even when ultraviolet rays are irradiated from the ultraviolet lamp 30 into the chamber 23, the ultraviolet rays are prevented from being directly irradiated to the cultures cultivated in the cultivating containers 41. Therefore, no adverse effect is imposed on the cultivation of the cultures.

[E] Fifth Embodiment

Figure 13:
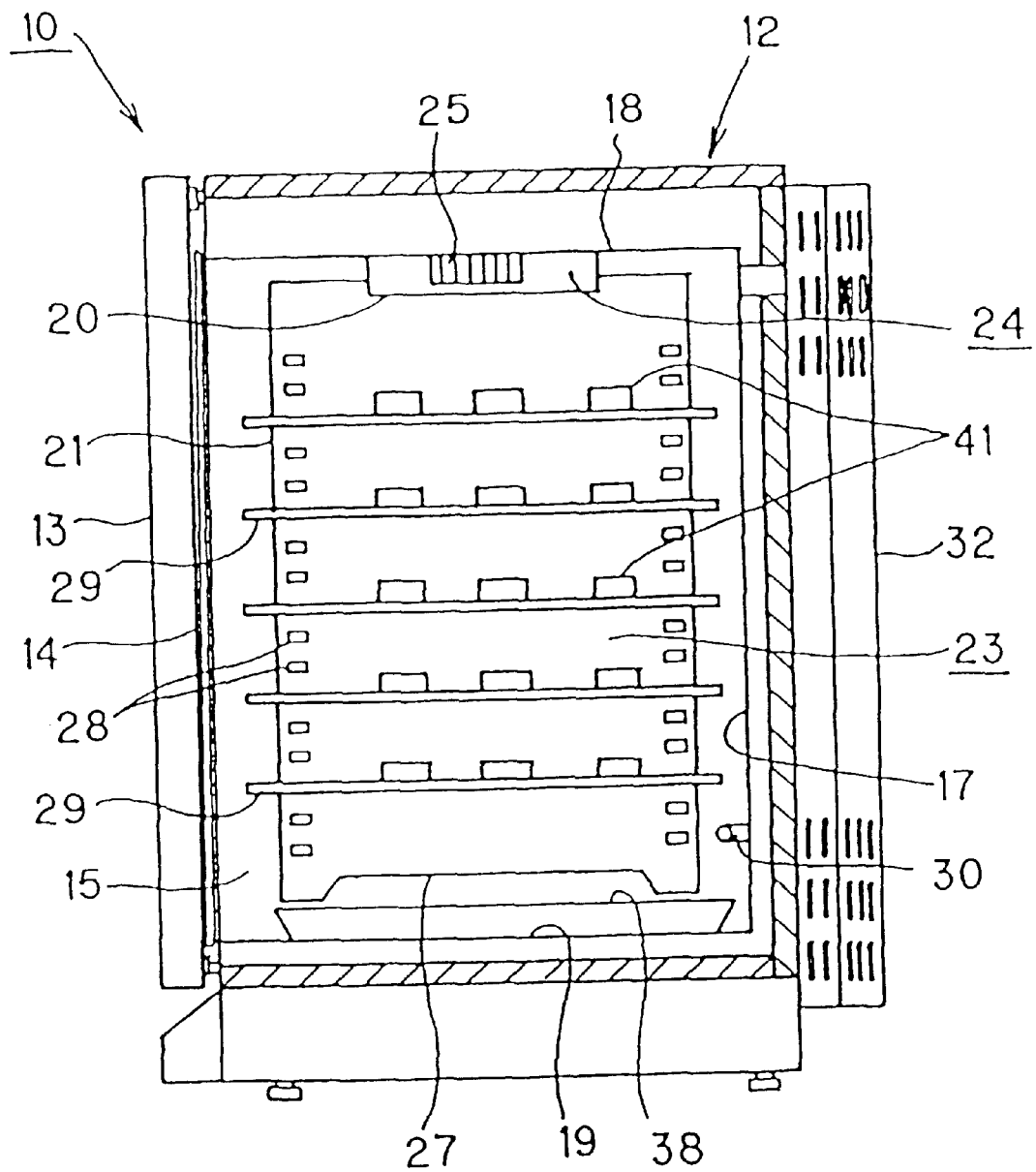
FIG. 13 is an explanatory diagram (side sectional view) showing a carbon dioxide gas ($CO_2$) incubator to which a fifth embodiment of the cultivating apparatus of the present invention is applied when the door of the incubator is closed.
Figure 14:
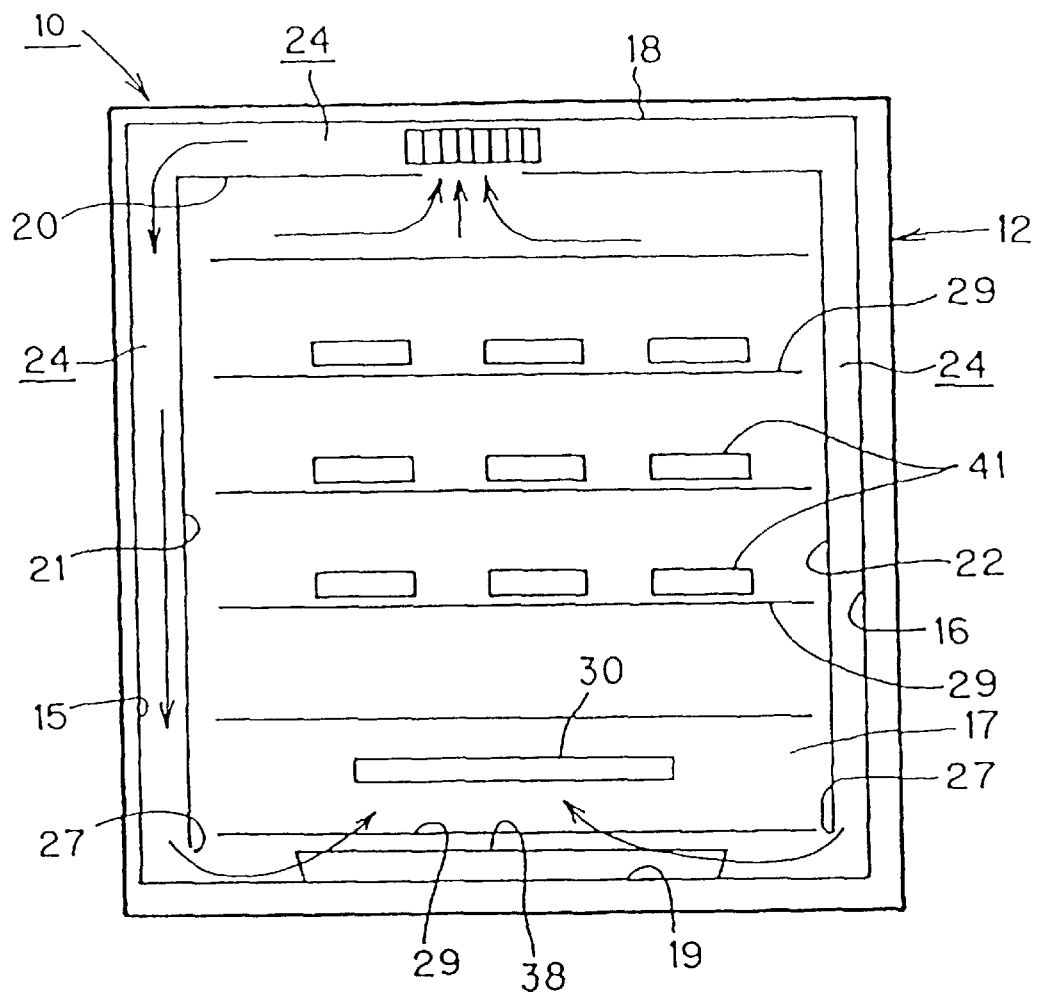
FIG. 14 is a front view showing the incubator of FIG. 13 when the door of the incubator is opened.

FIG. 13 is a side sectional view showing a carbon dioxide gas ($CO_2$) incubator to which a fifth embodiment of the cultivating apparatus of the present invention is applied, and FIG. 14 is a front view showing the incubator of FIG. 13 when the outer door is opened. In the fifth embodiment, the same reference elements as the first to fourth embodiments are represented by the same reference numerals, and the duplicative description thereof is omitted.

In the cultivating apparatus 10 of this embodiment, the ultraviolet lamp 30 is disposed in the chamber 23, and it is mounted nearly above the water dish 38 on the back wall 17 so that the ultraviolet rays from the ultraviolet lamp 30 are irradiated to the water in the water dish 38.

The fifth embodiment is the same as the fourth embodiment in that the cultivating containers 41 stocking the cultures are formed of ultraviolet-ray intercepting material through which no ultraviolet ray is transmitted, or designed so that the surface or back surface of the constituent material such as glass material or the like is coated with ultraviolet-ray intercepting coating or the like. Therefore, no ultraviolet ray is directly irradiated to the cultures cultivated in the cultivating containers 41.

Accordingly, the fifth embodiment of the present invention has not only the effects (1), (3) to (7) of the first embodiment, but also the effects (8) and (10) of the third embodiment and the effect of the fourth embodiment (11).

The present invention is not limited to the above embodiments, and various modifications may be made without departing from the subject matter of the present invention.

For example, the top plate portion 20 and the side plates 21 and 22 may be designed so as to be freely detachable from the main body of the apparatus. In this case, if the top plate portion 20 and the side plates 21, 22 are detached from the apparatus and the ultraviolet lamp 30 is turned on, the wall surfaces of the top wall 18 and the side walls 15, 16 can be subjected to the sterilization treatment.

Further, it may be adopted that the ultraviolet lamp 30 is not disposed in the gas circulating passage 24, but disposed on the outer wall of the top wall 18 as in the case of the second embodiment, and the top wall 18 is covered by a shielding plate (not shown) from the lower side to prevent the ultraviolet rays of the ultraviolet lamp 30 from being directly irradiated to the inside of the chamber 23 (cultivating containers 41) by the shielding plate. In this case, normal cultivating containers 11 may be used in place of the special cultivating containers which are formed of ultraviolet-ray intercepting material.

Likewise, the shielding plate may be provided to the fifth embodiment to prevent the ultraviolet rays of the ultraviolet lamp 30 from being directly irradiated into the chamber 23 (cultivating containers 41). At this time, if the shielding plate is formed of a reflection plate as in the case of the third embodiment, the above effect (9) can be achieved.

Further, it may be adopted that the gas circulating passage 24 is extended to the outside of the main body 12 of the apparatus by using a duct or the like and the ultraviolet lamp 30 is disposed in the duct to sterilize germs contained in gas flowing through the duct and guide the sterilized gas into the chamber 23.

In a case where cultures are very weak to ultraviolet rays, the cultivating containers 41 of the fourth embodiment may be disposed in the chamber 23 of the incubator 10 in place of the cultivating containers of the first embodiment. On the other hand, in a case where cultures are very strong to ultraviolet rays, the cultivating containers 11 of the first embodiment may be disposed in the chamber 23 of the incubator 10 in place of the cultivating containers 41 of the fourth embodiment.

Still further, the controller 32 may control the ultraviolet lamp 30 to be turned on when the opening operation of the outer door 13 is carried out to sterilize various germs contained in gas flowing into the chamber 23, and turned out after a predetermined time (for example, 5 minutes) elapses from the closing operation of the outer door 13.

The ultraviolet lamp 30 may be disposed in the space between the side wall 15 and the side plate 21 or between the side wall 16 and the side plate 22 in the gas circulating passage 24.

As described above, the cultivating apparatus of the present invention is provided with the sterilizing lamp for sterilizing various germs contained in gas inside the apparatus. Therefore, the germs contained in the gas can be easily sterilized and the contamination of the germs into the cultures can be surely prevented.

What is claimed is:

1. A cultivating apparatus designed so that cultivating containers for cultivating cultures can be mounted therein and the inside of the apparatus is hermetically sealed by closing a door of said apparatus to cultivate the cultures, characterized by including a sterilizing lamp for emitting light for sterilizing germs contained in the gas in said apparatus, said apparatus further including a water container for stocking humidifying water, wherein said sterilizing lamp is disposed with respect to the surface of the humidifying water to sterilize the same.

2. The cultivating apparatus as claimed in claim 1, further including a reflection member which is disposed so as to cover said sterilizing lamp and prevent the light from being irradiated from said sterilizing lamp to said cultivating containers.

3. The cultivating apparatus as claimed in claim 1, wherein said sterilizing lamp is disposed in said apparatus so as to allow irradiation of light from said sterilizing lamp to the inside of said apparatus.

4. The cultivating apparatus as claimed in claim 1, wherein said cultivating containers are designed to intercept light irradiated from said sterilizing lamp.

5. The cultivating apparatus as claimed in claim 1, wherein said sterilizing lamp is turned on/out interlockingly with an open/close operation of said door.

6. The cultivating us as claimed in claim 1, wherein said sterilizing lamp is an ultraviolet lamp.

7. The cultivating apparatus as claimed in claim 6, wherein said ultraviolet lamp is designed so that light of 200 nm or less in wavelength is cut off.

* * * * *